(12) United States Patent
Bryant

(10) Patent No.: US 6,352,603 B1
(45) Date of Patent: Mar. 5, 2002

(54) LOOP ATTACHMENT TO APERTURED DEVICE

(75) Inventor: Julian Bryant, Leeds (GB)

(73) Assignee: Neoligaments Limited, Leeds (GB)

( * ) Notice: Subject to any disclaimer, the term of this patent is extended or adjusted under 35 U.S.C. 154(b) by 0 days.

(21) Appl. No.: 09/423,580

(22) PCT Filed: Mar. 8, 1999

(86) PCT No.: PCT/GB99/00591

§ 371 Date: Nov. 10, 1999

§ 102(e) Date: Nov. 10, 1999

(87) PCT Pub. No.: WO99/47079

PCT Pub. Date: Sep. 23, 1999

(30) Foreign Application Priority Data

Mar. 13, 1998 (GB) .............................. 9805238
Mar. 18, 1998 (GB) .............................. 9805598

(51) Int. Cl.$^7$ ................................. A61F 2/08
(52) U.S. Cl. ................... 156/148; 156/173; 156/175; 156/308.2; 156/393; 623/13.11; 623/13.14
(58) Field of Search ............... 156/148, 173, 156/175, 393, 308.2; 623/13.11, 13.12, 13.14, 13.19, 13.2; 242/360, 362, 364.11; 59/84, 3

(56) References Cited

U.S. PATENT DOCUMENTS 3,153,898 A * 10/1964 Gerhardt ..................... 59/84
5,306,301 A 4/1994 Graf et al. ................ 623/13.11
5,571,184 A * 11/1996 DeSatnick .................... 623/13
5,607,478 A 3/1997 Lentz et al. .............. 623/23.69
5,769,894 A * 6/1998 Ferragamo ................... 623/13

FOREIGN PATENT DOCUMENTS

| CH | 664 890 | 4/1988 |
| WO | WO 96/29029 | 9/1996 |

* cited by examiner

Primary Examiner—Jeff H. Aftergut
Assistant Examiner—Todd J. Kilkenny
(74) Attorney, Agent, or Firm—Merchant & Gould P.C.

(57) ABSTRACT

A winding device (10) for use in the simultaneous formation and attachment of a loop (11) to an apertured implantable device (12), in which the loop is formed from a loosely structured fiber bundle of twisted yarn, and the device (12) has first and second apertures (13, 14) through which the loop can be taken, and comprising: withdrawing a leading end of yarn from a yarn supply (15, 18, 21) and feeding the leading end through the first aperture (13) in one direction, and through the second aperture (14) in an opposite direction; taking the leading end of yarn away from the device (12) and along a guide path formed by rotatable capstans (16) so as to form a basic loop; withdrawing further yarn from the supply simultaneously with applying movement of the basic loop along the guide path so as to apply successive loop turns to the basic loop and therefore from a progressively increasing loop core; and applying relative twists between the loop core and each successive loop turn so as to form a cohesive looped fiber bundle attached to the device. The method is particularly suitable for use in the automated production and attachment of a loop to an implantable device (12) used in the implantation of a prosthetic ligament.

16 Claims, 2 Drawing Sheets

LOOP ATTACHMENT TO APERTURED DEVICE

This invention is concerned generally with the attachment of a loop to an apertured device e.g. an implantable device for use in the itmplantation of a prosthetic ligament.

In the implantation of a prosthetic ligament in a bone joint e.g. the knee joint between tibial and femoral components, it is usual to drill tunnels through the bones, and to pull the prosthetic ligament through the tunnels until a required position is reached within the joint, followed by suitable anchoring of the ligament against linear movement in either direction. The anchoring may involve use of bone staples or other intrusive fixations, which attach tensile elements (connected to each end of the ligament) to suitable bone sites adjacent to the mouths of the bone tunnels.

Prosthetic ligaments can be made of synthetic material, provided that it is of suitable implantable nature, and which may be woven, although autogenous tissue harvested from the patient is the more popular method.

One more recent endoscopic technique which has been developed in ACL reconstruction (anterior cruciate ligament reconstruction), involves use of an attachment device which serves both to guide the implantation of the ligament, and to secure one end of the ligament against axial movement in one direction, but the attachment device is of such a construction that it does not need to anchor itself in position by physical intrusion into the bone.

The attachment device used in the technique provides easy guidance of the ligament, by forming the lead element of a trailing implantation system, and which passes through the usual drilled-out bone tunnels, and then upon exiting of the lead element from an upper mouth of one of the tunnels i.e. when it projects upwardly out of the femoral component, a simple manipulation of the device causes it to overlie the mouth of the tunnel, and thereby provide tensile restraint for the ligament end of the now implanted ligament to which it is attached.

The attachment device therefore is capable of being manipulated between a pulling position, in which it has reduced lateral extent relative to the pulling direction, and to an anchoring position in which it has maximum lateral extent relative to the pulling direction.

This known attachment device (known as an endobutton) comprises a small metal bar which is about 12 mm in length, 4 mm wide and 1.5 mm in thickness, and has a row of four circular holes extending through it, of which the two outermost holes serve for attachment of two separate pulling sutures, and the inner pair of holes serve to attach the metal bar to the trailing ligament via a further set of sutures. The set of pulling sutures is taken first through the lower end of the lowermost bone tunnel in the tibial component and then passes upwardly through the bone tunnel in the femoral component, and pulls the trailing ligament system behind it. In practice only one of the sutures has tension applied to it sufficient to pull the metal bar behind it with the bar manipulating itself to take-up the pulling position of reduced lateral projection, and to be pulled lengthwise through the tunnels. Since the bar orientates itself so that its longitudinal axis aligns itself with the pulling direction, the diameter of the final passage drilled through the femoral component can be reduced, compared with the larger diameter of the tunnel which is formed so as to receive the implanted ligament. This final passage therefore can have a diameter of slightly more only than the maximum transverse dimension of the bar (4 mm). Upon exiting from the femoral component, the other pulling suture is then operated so as to manipulate the bar to take-up a transverse position in which its longitudinal axis is generally perpendicular to the passage whereby it can overlie the exit mouth of the small diameter passage. Downward tension applied to the trailing assembly attached to the bar then anchors the attachment bar in position in a non-intrusive manner with respect to the surrounding bone.

The trailing assembly which follows the pulling-through of the attachment bar usually comprises (a) further sutures which are taken through the central pair of holes in the bar, and then connected together to complete the formation of a loop by knotting together of the ends of the sutures, and (b) the prosthetic ligament which is attached to the looped sutures in any convenient manner.

In the case of harvested tissue which comprises tendon material and boney material (plugs) attached at each end of the tendon material, the sutures are taken through holes formed in one of the bone plugs and then knotted to complete the formation of the attachment loop.

The present invention is concerned with the use of different material to form an attached loop to the existing use of sutures knotted together, as referred to above, and utilises flexible and implantable material assembled from a loosely structured fibre bundle of twisted yarn. In particular, the present invention is concerned with a method and device for the simultaneous formation and attachment of the loop (comprising a loosely structured fibre bundle) to an apertured device, so as to speed-up the attachment of the loop and thereby derive the benefits of mass production techniques, compared with existing purely manual manipulations which are employed in order to attach a loop to an apertured device.

According to one aspect of the invention there is provided a method for the simultaneous formation and attachment of a loop to an apertured device, in which the loop is formed from a loosely structured fibre bundle of twisted yarn, and the device has first and second apertures through which the loop can be taken, in which the method comprises:

withdrawing a leading end of yarn from a yarn supply and feeding the leading end through the first aperture in one direction, and through the second aperture in an opposite direction;

taking the leading end of yarn away from the device and along a guide path so as to form a basic loop;

withdrawing further yarn from the supply simultaneously with applying movement of the basic loop along the guide path so as to apply successive loop turns to the basic loop and therefore form a progressively increasing loop core; and, applying relative twist between the loop core and each successive loop turn so as to form a cohesive looped fibre bundle attached to the device.

The method of the invention therefore automates the production of a device with attached loop, and allows a greatly increased rate of manufacture as compared with purely manual manipulation methods used to date.

Preferably, the initial "threading through" of the yarn through the device is carried out by manual manipulation, and the subsequent completion of the basic loop, but thereafter the operation can be automatic.

The basic loop can be completed by any suitable technique, and conveniently the leading end is joined to the trailing end of the loop (having just issued from the yarn supplied) by heat fusion e.g. light application of a heating head to the leading end. The basic loop can then be caused to carry out successive orbits of its closed path while further loop turns are applied thereto, and the progressively increasing loop core also is then caused to carry out successive orbits while further loop turns are applied thereto.

Preferably, rotatable capstans are arranged along the closed path, and engage the basic loop (and the increasing loop core), Lo drive it along the closed loop while further yarn is withdrawn from the supply.

Relative twist between the loop core and successive loop turns may be obtained by one of three techniques, namely:

1. causing the loop core to pass through a bobbin supply of yarn (forming part of the closed guide path), and rotating the bobbin about this portion of the closed path while yarn is withdrawn;
2. withdraw yarn off the end of a stationary bobbin (PIRN); and,
3. applying twisting movement to the loop core as it moves along the closed path, simultaneously with application of yarn from the supply to the circumference of the rotating loop core.

According to a further aspect of the invention, there is provided a winding device for the simultaneous formation and attachment of a loop to an apertured device, in which the loop is formed from a loosely structured fibre bundle of twisted yarn, and the device has first and second apertures through which the loop can be taken, in which the winding device comprises:

means for holding the device stationary;

a holder for holding a supply of yarn;

a guide path for allowing the leading end of yarn to be withdrawn from the supply and to pass through the first aperture in the device in one direction and through the second aperture in an opposite direction, and thereafter moving away from the device so as to form a basic loop;

means for applying movement of the basic loop along the guide path simultaneously with withdrawal of further yarn from the supply so as to apply successive loop turns to the basic loop and thereby form a progressively increasing loop core; and, means for applying relative twist between the loop core and each successive loop turn so as to form a cohesive looped fibre bundle attached to the device.

Preferred embodiments of method according to the invention will now be described in detail, (and also preferred embodiments of winding device according to the invention), for use in the simultaneous formation and attachment of a loop to an apertured device will now be described in detail, with reference to the accompanying drawings, in which.

Figure 1:
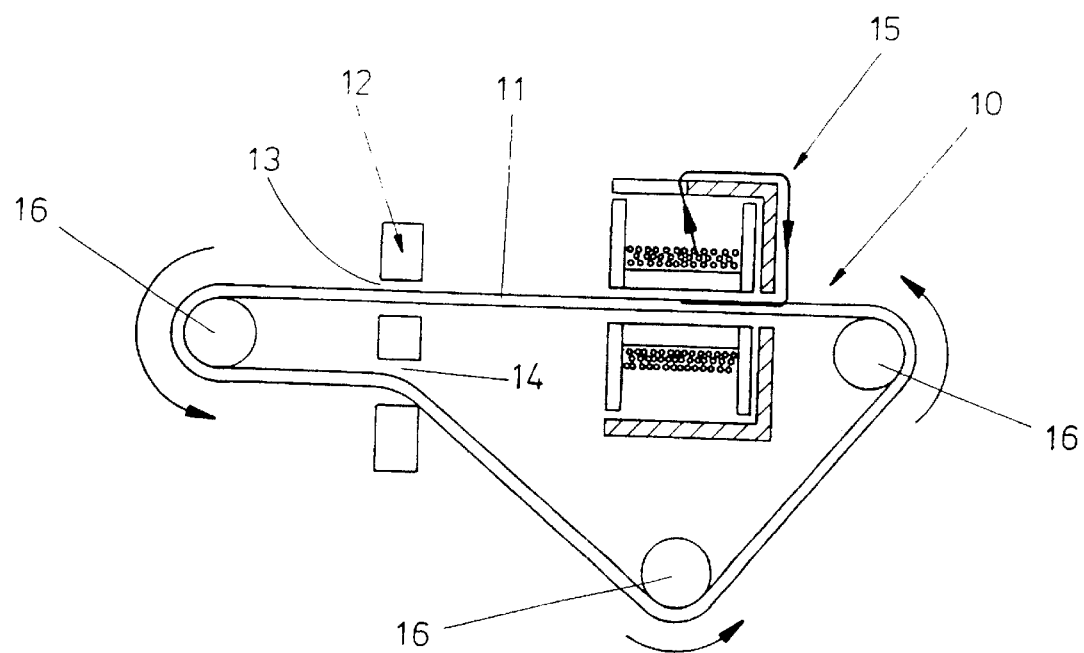
FIG. 1 is a schematic side view of a first embodiment of the invention, in which a rotating bobbin serves both to supply yarn to form a continuous loop attached to the device, simultaneously with application of twist to the withdrawn yarn to form successive cohesive loop turns.

Referring now to the drawings, there will be described embodiments of method for the simultaneous formation and attachment of a loop to an apertured implantable device, in which the loop is formed from a loosely structured fibre bundle of twisted yarn, and the implantable device has first and second apertures through which the loop can be taken. There will also be described preferred embodiments of winding device for carrying out the method.

In general terms, a yarn supply is provided e.g. a bobbin, and a leading end of the yarn is withdrawn from the supply and is then fed through the first aperture in the implantable device in one direction and through the second aperture in an opposite direction. The leading end of yarn is then taken away from the implantable device and along a guide path so as to form a basic loop; further yarn is withdrawn from the supply simultaneously with applying movement of the basic loop along the guide path so as to apply successive loop turns to the basic loop and thereby form a progressively increasing loop core; and relative twist is applied between the loop core and each successive loop turn so as to form a cohesive looped fibre bundle attached to the implantable device.

Referring first to FIG. 1 of the drawings, this shows a first embodiment of winding device, designated generally by reference 10, and which is capable of the simultaneous formation and attachment of a loop 11 to an apertured implantable device 12. The device 12 has first and second apertures 13 and 14 through which the loop 11 can be taken, as will be described in more detail below.

The loop 11 is derived from a yarn supply which, in the embodiment illustrated, comprises a rotatable bobbin 15. The yarn carried by the bobbin 15 is formed from 96 filaments at 550 decitex, and having 48 twists per meter.

A leading end of yarn is withdrawn from the bobbin 15, and is then fed, preferably by manual manipulation, through the first aperture 13 in one direction and through the second aperture 14 in an opposite direction. The leading end is then moved in a direction away from the implantable device 12, and along a guide path so as to form a basic loop. The guide path is determined by provision of three guides, taking the form of rotatable capstans 16. The guide path is also determined by the location of the rotatable bobbin 15, through the middle of which the loop 11 extends, and about which the bobbin 15 is rotatable. The guide path is also determined by the position of the apertures 13 and 14, which in turn are determined by the particular fixed location on the winding device for the device 12.

In order to complete the formation of a basic loop i.e. after the leading end has completed an "orbit" around the closed path, the leading end is joined to the trailing end issuing from the bobbin 15 by any convenient means, such as heat fusion. This completed basic loop is then ready to carry out further orbits along the closed path, while further loop turns are applied thereto.

Therefore, further yarn is withdrawn from the supply bobbin 15 simultaneously with application of movement to the basic loop along the guide path so as to apply successive loop turns to the basic loop and thereby form a progressively increasing loop core. The application of movement to the basic loop core is achieved by application of drive to the capstans 16.

Relative twist is applied between the loop core and each successive loop turn so as to form a cohesive looped fibre bundle attached to the implantable device 12.

In the embodiment shown in FIG. 1, this is achieved by having the bobbin 15 effectively straddling the loop 11, and then rotation is applied to the bobbin 15 simultaneously with advancing movement of the basic loop 11 along the closed guide path. Successive loop turns are applied, with each complete movement along the closed path, until a required number of loop turns have been formed, which might, in a typical example, be about 35 to 40. By virtue of the application of relative twisting movement, the loop turns form a cohesive loosely structured bundle, which is particularly suitable for use with an implantable device.

The arrangement shown in FIG. 1, whereby relative twisting is applied by provision of the rotating bobbin 15, is one preferred means of applying relative rotation. However, other means may be employed, as will now be described below with reference to FIGS. 2 and 3. Parts corresponding with those already described are given the same reference numerals, and therefore need not be described in detail again.

Figure 2:
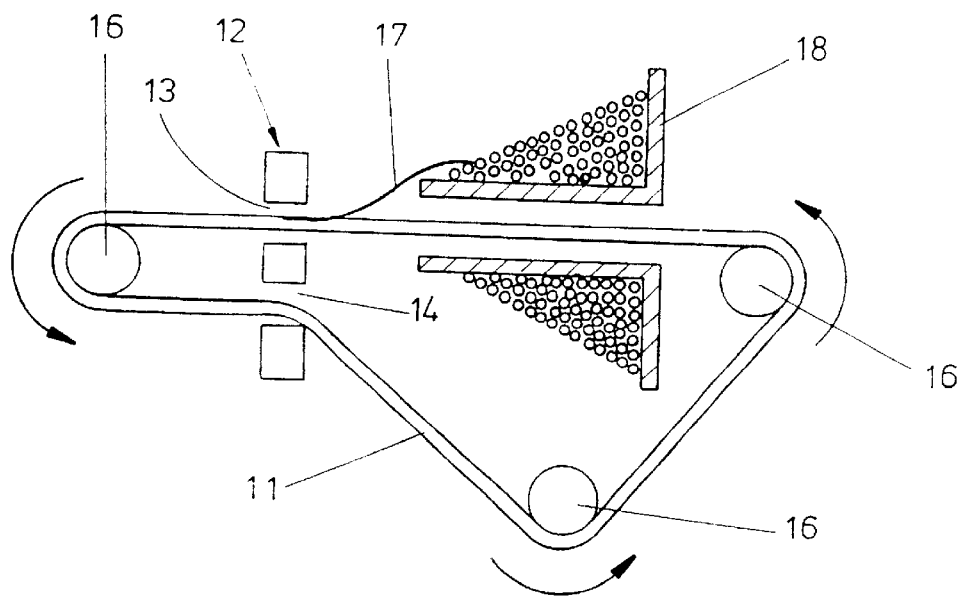
FIG. 2 is a schematic side view showing an alternative means of withdrawing yarn, and applying relative twist between the loop core being formed and the withdrawn yarn from the supply; and, FIG. 3 is a schematic side view illustration of a third embodiment which allows simultaneous withdrawal of yarn, and application of relative twist between the withdrawn yarn and the loop core.

Referring to FIG. 2, the yarn supply is derived from a conical winding of yarn 17 on a stationary bobbin 18 (known as a PIRN), the yarn 17 can be drawn off the end of the bobbin 18 and simultaneously wrap itself around the loop 11 as the latter is driven along its closed path by the rotating capstans 16.

Figure 3:
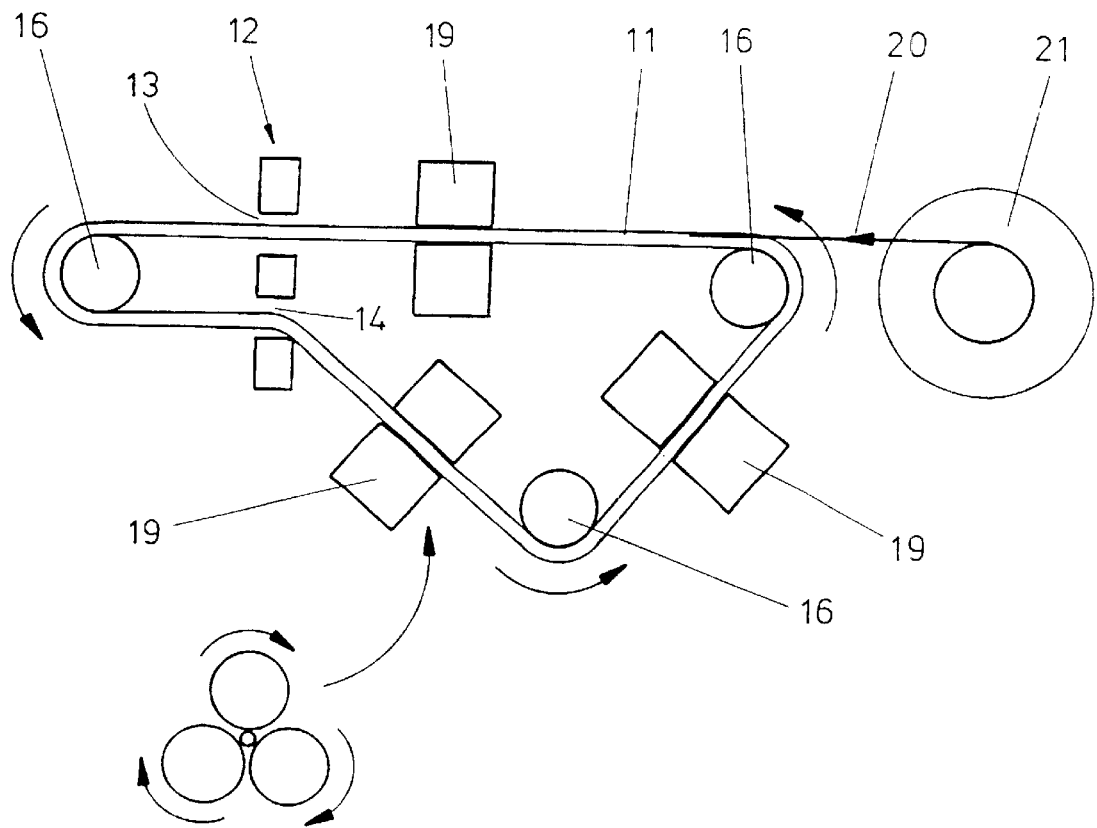

A further alternative means of applying relative twisting action is shown in FIG. 3, in which the entire loop core is caused to be twisted about its axis, during each orbiting movement of the loop 11 along its closed path. Yarn 20 is withdrawn from supply device 21, and three separate twisting devices 19 are arranged along the closed path, and apply twist to successive portions of the loop 11 as it moves along the path, simultaneously with the withdrawal of further yarn 20 from the supply device 21, to form cohesive successive loop turns. FIG. 3 also shows a detail of one of the typical twisting devices 19.

While the embodiments of the invention have been described in relation to the formation and attachment of a loop to an apertured implantable device, it should be understood that the invention has wider application, and can extend to use with other types of apertured device.

What is claimed is:

1. A method for simultaneous formation and attachment of a loop to an apertured device, in which the loop is formed from a loosely structured fibre bundle of twisted yarn, and the device has first and second apertures through which the loop can be taken, in which the method comprises:
    withdrawing a leading end of yarn from a yarn supply and feeding the leading end through the first aperture in one direction, and through the second aperture in an opposite direction;
    taking the leading end of yarn away from the device and along a guide path so as to form a basic loop;
    withdrawing further yarn from the supply simultaneously with applying movement of the basic loop along the guide path so as to apply successive loop turns to the basic loop and therefore form a progressively increasing loop core; and
    applying relative twist between the loop core and each successive loop turn so as to form a cohesive looped fibre bundle attached to the device.

2. A method according to claim 1, in which the initial threading of the yarn through the device and the subsequent completion of the basic loop are carried out by manual manipulation, but thereafter is automatic.

3. A method according to claim 1, in which the basic loop is completed by joining the leading end to a trailing end of the loop, after issuing from the yarn supply, by heat fusion.

4. A method according to claim 1, in which rotatable capstans are arranged along a closed path, and engage the basic loop, and the increasing loop core, to drive it along a closed loop while further yarn is withdrawn from the supply.

5. A method according to claim 1, in which relative twist between the loop core and successive loop turns is obtained by causing the loop core to pass through a bobbin supply of yarn, forming part of a closed guide path, and rotating the bobbin about this portion of the closed path while yarn is withdrawn.

6. A method according to claim 1, in which relative twist between the loop core and successive loop turns is obtained by withdrawing yarn off the end of a stationary bobbin.

7. A method according to claim 1, in which relative twist between the loop core and successive loop turns is obtained by applying twisting movement to the loop core as it moves along a closed path, simultaneously with application of yarn from the supply to a circumference of the rotating loop core.

8. A winding device for simultaneous formation and attachment of a loop to an apertured device, in which the loop is formed from a loosely structured fibre bundle of twisted yarn, and the device has first and second apertures through which the loop can be taken, in which the winding device comprises:
    means for holding the device stationary;
    a holder for holding a supply of yarn;
    a guide path for allowing the leading end of yarn to be withdrawn from the supply and to pass through the first aperture in the device in one direction and through the second aperture in an opposite direction, and thereafter moving away from the device so as to form a basic loop;
    means for applying movement of the basic loop along the guide path simultaneously with withdrawal of further yarn from the supply so as to apply successive loop turns to the basic loop and thereby form a progressively increasing loop core; and
    means for applying relative twist between the loop core and each successive loop turn so as to form a cohesive looped fibre bundle attached to the device.

9. A winding device according to claim 8, in which rotatable capstans are arranged along the closed path, to engage the basic loop (the increasing loop core), and to drive it along a closed loop while further yarn is withdrawn from the supply.

10. A winding device according to claim 8, in which the holder comprises a rotatable bobbin, through which the loop core can be taken, so that relative twist between the loop core and successive loop turns can be obtained by rotation of the bobbin about the portion of the loop core passing through it while yarn is withdrawn.

11. A winding device according to claim 8, in which the holder comprises a stationary bobbin, from which yarn can be withdrawn in such a way that relative twist between the loop core and successive loop turns is obtained.

12. A winding device according to claim 8, in which the holder comprises a supply device from which yarn can be applied to circumference of the rotating loop core, and including means for applying twisting movement to the loop core as it moves along a closed path.

13. A winding device according to claim 12, in which said means for applying twisting movement to the loop core comprises one or more twisting device arranged along the closed path, and operative to apply twist to successive portions of the loop as it moves along the path, simultaneously with the withdrawal of further yarn from the supply device.

14. A method according to claim 1, in which the apertured device comprises an implantable device.

15. A winding device according to claim 8, in which the apertured device is an implantable device.

16. A winding device according to claim 8, wherein the apertured device is attached to a prosthetic ligament.

* * * * *

UNITED STATES PATENT AND TRADEMARK OFFICE
CERTIFICATE OF CORRECTION

PATENT NO. : 6,352,603 B1  
DATED : March 5, 2002  
INVENTOR(S) : Bryant

It is certified that error appears in the above-identified patent and that said Letters Patent is hereby corrected as shown below:

Column 5,  
Line 34, "fibre" should read -- fiber --  
Line 36, "in which" should read -- wherein --  
Line 50, "fibre" should read -- fiber --  
Line 59, "path," should read -- path --

Column 6,  
Line 11, "fibre" should read -- fiber --  
Line 13, "in which" should read -- wherein --  
Line 30, "fibre" should read -- fiber --  
Line 32, "path," should read -- path --  
Line 37, "bobbin," should read -- bobbin --  
Line 43, "bobbin," should read -- bobbin --

Signed and Sealed this

Twenty-third Day of July, 2002

Attest:

Attesting Officer

JAMES E. ROGAN  
Director of the United States Patent and Trademark Office